United States Patent
Banco et al.

(10) Patent No.: US 10,342,886 B2
(45) Date of Patent: Jul. 9, 2019

(54) EXTRUDED WAX MELT AND METHOD OF PRODUCING SAME

(71) Applicant: S. C. JOHNSON & SON, INC., Racine, WI (US)

(72) Inventors: Michael J. Banco, Racine, WI (US); Michael J. Fischer, Kenosha, WI (US)

(73) Assignee: S.C. JOHNSON & SON, INC., Racine, WI (US)

( * ) Notice: Subject to any disclaimer, the term of this patent is extended or adjusted under 35 U.S.C. 154(b) by 488 days.

(21) Appl. No.: 15/006,944

(22) Filed: Jan. 26, 2016

(65) Prior Publication Data
US 2017/0209611 A1    Jul. 27, 2017

(51) Int. Cl.
| | |
|---|---|
| *B29C 48/40* | (2019.01) |
| *A61L 9/012* | (2006.01) |
| *B29C 48/00* | (2019.01) |
| *B29C 48/76* | (2019.01) |
| *B29C 48/82* | (2019.01) |
| *B29C 48/85* | (2019.01) |
| *B29C 48/87* | (2019.01) |
| *B29C 48/88* | (2019.01) |
| *B29B 7/00* | (2006.01) |

(Continued)

(52) U.S. Cl.
CPC ............. *A61L 9/012* (2013.01); *B29B 7/005* (2013.01); *B29C 48/0022* (2019.02); *B29C 48/40* (2019.02); *B29C 48/76* (2019.02); *B29C 48/82* (2019.02); *B29C 48/85* (2019.02); *B29C 48/87* (2019.02); *B29C 48/911* (2019.02); *C11C 5/002* (2013.01); *C11C 5/008* (2013.01); *B29K 2091/00* (2013.01); *B29K 2105/16* (2013.01); *B29K 2511/00* (2013.01); *B29L 2031/74* (2013.01)

(58) Field of Classification Search
CPC ..... A61L 9/012; B29B 7/005; B29C 47/0066; B29C 47/40; B29C 47/76; B29C 47/845; B29C 47/864; B29C 47/8815; C11C 5/002; C11C 5/008
See application file for complete search history.

(56) References Cited

U.S. PATENT DOCUMENTS

| | | |
|---|---|---|
| 1,954,659 A | 4/1934 | Will |
| 2,422,990 A | 6/1947 | Spanier |

(Continued)

FOREIGN PATENT DOCUMENTS

| | | |
|---|---|---|
| EP | 706789 A1 | 4/1996 |
| EP | 723776 A1 | 7/1996 |

(Continued)

OTHER PUBLICATIONS

"Conveyer Belt Take-Off", C. W. Brabender, Jun. 23, 2014, accessed at cwbrabender.conn on Jun. 27, 2018. (Year: 2014).*

(Continued)

*Primary Examiner* — Anthony Calandra
*Assistant Examiner* — Jamel M Nelson
(74) *Attorney, Agent, or Firm* — Quarles & Brady LLP

(57) ABSTRACT

A wax melt blank is produced with an extrusion process and intended to later be cut to length into individual wax melts. The wax melt blank includes at least about fifty percent by weight of wax, a fragrance, and up to about fifty percent by weight of a filler. The wax, the fragrance, and the filler are homogeneously dispersed within the wax melt blank.

16 Claims, 5 Drawing Sheets

(51) Int. Cl.
*C11C 5/00* (2006.01)
*B29K 91/00* (2006.01)
*B29K 105/16* (2006.01)
*B29K 511/00* (2006.01)
*B29L 31/00* (2006.01)

(56) References Cited

U.S. PATENT DOCUMENTS

| | | |
|---|---|---|
| 2,434,557 A | 1/1948 | Fox, Jr. et al. |
| 2,439,506 A | 4/1948 | Christian |
| 2,461,723 A | 2/1949 | Cowan |
| 3,002,221 A | 10/1961 | Wright |
| 3,324,034 A | 6/1967 | Merz et al. |
| 3,417,040 A | 12/1968 | Kremer |
| 3,519,586 A | 7/1970 | Combs et al. |
| 3,556,403 A | 1/1971 | Manginelli |
| 3,630,697 A | 12/1971 | Cassar et al. |
| 3,680,995 A | 8/1972 | Frazier, Jr. et al. |
| 3,698,640 A | 10/1972 | Stanciu |
| 3,702,495 A | 11/1972 | Renoe |
| 3,779,785 A | 12/1973 | Stiles et al. |
| 3,804,744 A | 4/1974 | Fera |
| 3,841,813 A | 10/1974 | Stanciu |
| 3,998,922 A | 12/1976 | Weiss |
| 4,002,706 A | 1/1977 | Pretorius |
| 4,017,231 A | 4/1977 | Karlsson |
| 4,110,261 A | 8/1978 | Newland |
| 4,396,673 A | 8/1983 | Ball et al. |
| 4,405,509 A | 9/1983 | Rogers et al. |
| 4,446,087 A | 5/1984 | Templin |
| 4,515,909 A | 5/1985 | Sawano et al. |
| 4,614,625 A | 9/1986 | Wilson |
| 4,714,496 A | 12/1987 | Luken, Jr. et al. |
| 4,813,975 A | 3/1989 | Poulina et al. |
| 4,934,921 A | 6/1990 | Shieh |
| 4,948,359 A | 8/1990 | Yasui |
| 4,971,547 A | 11/1990 | Nett, Jr. et al. |
| 5,037,874 A | 8/1991 | Nuttens et al. |
| 5,066,216 A | 11/1991 | Kowtko et al. |
| 5,205,969 A | 4/1993 | Nett, Jr. et al. |
| 5,294,251 A | 3/1994 | Urena |
| 5,578,089 A | 11/1996 | Elmastoy |
| 5,773,039 A | 6/1998 | Jones |
| 5,861,128 A | 1/1999 | Vick et al. |
| 5,869,555 A | 2/1999 | Simmons et al. |
| 5,916,949 A | 6/1999 | Shapero |
| 5,919,423 A | 7/1999 | Requejo et al. |
| 5,955,034 A | 9/1999 | Zaunbrecher |
| 5,959,129 A | 9/1999 | van Dam et al. |
| 5,972,319 A | 10/1999 | Linn et al. |
| 6,019,804 A | 2/2000 | Requejo et al. |
| 6,036,925 A | 3/2000 | Adams et al. |
| 6,063,144 A | 5/2000 | Caldaza et al. |
| 6,086,644 A | 7/2000 | Nakatsu et al. |
| 6,106,597 A | 8/2000 | Starks et al. |
| 6,110,880 A | 8/2000 | VerStrate |
| 6,111,055 A | 8/2000 | Berger et al. |
| 6,129,771 A | 10/2000 | Ficke et al. |
| 6,214,918 B1 | 4/2001 | Johnson |
| 6,224,641 B1 | 5/2001 | Matzat et al. |
| 6,267,970 B1 | 7/2001 | Matesevac |
| 6,284,007 B1 | 9/2001 | Tao |
| 6,306,353 B2 | 10/2001 | Freeman et al. |
| 6,380,462 B1 | 4/2002 | Kridl |
| 6,428,753 B2 | 8/2002 | Freeman |
| 6,440,349 B1 | 8/2002 | Johnson |
| 6,497,735 B2 | 12/2002 | Tao |
| 6,500,218 B1 | 12/2002 | Fan |
| 6,503,077 B2 | 1/2003 | Orth et al. |
| 6,503,285 B1 | 1/2003 | Murphy |
| 6,533,828 B1 | 3/2003 | Calzada |
| 6,544,303 B2 | 4/2003 | Calzada |
| 6,599,334 B1 | 7/2003 | Anderson |
| 6,623,855 B2 | 9/2003 | Hsia |
| 6,645,261 B2 | 11/2003 | Murphy et al. |
| 6,730,137 B2 | 5/2004 | Pesu et al. |
| 6,755,641 B1 | 6/2004 | Nakanishi |
| 6,758,869 B2 | 7/2004 | Roeske |
| 6,770,104 B2 | 8/2004 | Murphy |
| 6,773,469 B2 | 8/2004 | Murphy |
| 6,776,808 B2 | 8/2004 | Foster |
| 6,797,020 B2 | 9/2004 | Murphy |
| 6,805,855 B2 | 10/2004 | Mattai et al. |
| 6,824,572 B2 | 11/2004 | Murphy |
| 6,852,140 B1 | 2/2005 | Roeske |
| 7,018,432 B2 | 3/2006 | Moussouni |
| 7,086,852 B2 | 8/2006 | Nakanishi |
| 7,128,766 B2 | 10/2006 | Murphy et al. |
| 7,148,284 B2 | 12/2006 | Morrison et al. |
| 7,160,337 B2 | 1/2007 | Williams et al. |
| 7,192,457 B2 | 3/2007 | Murphy et al. |
| 7,217,301 B2 | 5/2007 | Murphy et al. |
| 7,220,288 B2 | 5/2007 | D'Amico et al. |
| 7,259,219 B2 | 8/2007 | Rosen et al. |
| 7,267,743 B2 | 9/2007 | Borsinger et al. |
| 7,291,187 B2 | 11/2007 | Welch et al. |
| 7,294,189 B2 | 11/2007 | Wantling |
| 7,335,372 B2 | 2/2008 | Hannich et al. |
| 7,387,649 B2 | 6/2008 | Tao |
| 7,410,513 B2 | 8/2008 | Requejo et al. |
| 7,420,008 B2 | 9/2008 | Bloom |
| 7,445,648 B2 | 11/2008 | Hudson et al. |
| 7,449,504 B2 | 11/2008 | Richter |
| 7,462,205 B2 | 12/2008 | Murphy |
| 7,510,584 B2 | 3/2009 | Cap |
| 7,549,396 B2 | 6/2009 | Hurwitz et al. |
| 7,569,084 B2 | 8/2009 | Tao et al. |
| 7,588,607 B1 | 9/2009 | Cap |
| 7,601,184 B2 | 10/2009 | Tischendorf |
| 7,637,968 B2 | 12/2009 | Murphy |
| 7,671,122 B2 | 3/2010 | Odajima et al. |
| 7,713,314 B2 | 5/2010 | Jones |
| 7,731,767 B2 | 6/2010 | Tao |
| 7,767,299 B2 | 8/2010 | Easter |
| 7,833,294 B2 | 11/2010 | Murphy |
| 7,833,515 B2 | 11/2010 | Corzani et al. |
| 7,842,746 B2 | 11/2010 | Bloom |
| 7,959,689 B2 | 6/2011 | Cagle |
| 8,021,443 B2 | 9/2011 | Murphy et al. |
| 8,070,833 B2 | 12/2011 | Murphy |
| 8,070,834 B2 | 12/2011 | Tao |
| 8,074,605 B2 | 12/2011 | Hurwitz |
| 8,137,418 B2 | 3/2012 | Tao |
| 8,157,873 B2 | 4/2012 | Murphy |
| 8,168,682 B2 | 5/2012 | O'Connor |
| 8,173,733 B2 | 5/2012 | Kashihara |
| 8,202,329 B2 | 6/2012 | Murphy et al. |
| 8,273,826 B2 | 9/2012 | Walton |
| 8,404,003 B2 | 3/2013 | Tao et al. |
| 8,439,668 B2 | 5/2013 | Ambroggio |
| 8,529,924 B2 | 9/2013 | Murphy et al. |
| 8,551,194 B2 | 10/2013 | Uptain et al. |
| 8,603,197 B2 | 12/2013 | Lemke et al. |
| 8,652,221 B2 | 2/2014 | Uptain et al. |
| 8,685,118 B2 | 4/2014 | Murphy |
| 8,784,984 B2 | 7/2014 | Grey |
| 8,940,090 B2 | 1/2015 | Lemke et al. |
| 9,056,302 B2 | 6/2015 | Jung et al. |
| 2002/0002792 A1 | 1/2002 | Freeman et al. |
| 2002/0019510 A1 | 2/2002 | Orth et al. |
| 2003/0024997 A1 | 2/2003 | Welch et al. |
| 2003/0105183 A1 | 6/2003 | Sharak |
| 2003/0195272 A1 | 10/2003 | Harwell et al. |
| 2004/0146537 A1 | 7/2004 | Radhakrishnan et al. |
| 2004/0234469 A1 | 11/2004 | O'Connor et al. |
| 2005/0158679 A1 | 7/2005 | Chen et al. |
| 2006/0000139 A1 | 1/2006 | Biggs |
| 2006/0013842 A1 | 1/2006 | Matkin et al. |
| 2006/0263732 A1 | 11/2006 | Fiwek |
| 2006/0272199 A1 | 12/2006 | Licciardello et al. |
| 2007/0006521 A1 | 1/2007 | Licciardello et al. |
| 2007/0065379 A1 | 3/2007 | Biatry et al. |
| 2007/0094916 A1 | 5/2007 | Burkhamer et al. |
| 2007/0108759 A1 | 5/2007 | D'Amico |

(56) References Cited

U.S. PATENT DOCUMENTS

| | | |
|---|---|---|
| 2007/0144058 A1 | 6/2007 | Chen et al. |
| 2007/0169404 A1 | 7/2007 | Cagle |
| 2007/0282000 A1 | 12/2007 | Murphy et al. |
| 2008/0132625 A1 | 6/2008 | Niehaus et al. |
| 2008/0138753 A1 | 6/2008 | Tao et al. |
| 2008/0282601 A1 | 11/2008 | Luttke |
| 2008/0292855 A1 | 11/2008 | Manderfield et al. |
| 2008/0307696 A1 | 12/2008 | Wu et al. |
| 2009/0041820 A1 | 2/2009 | Wu et al. |
| 2009/0062427 A1 | 3/2009 | Tornow |
| 2009/0217568 A1 | 9/2009 | Murphy et al. |
| 2010/0024281 A1 | 2/2010 | Lemke et al. |
| 2010/0044924 A1 | 2/2010 | Cap |
| 2010/0063173 A1 | 3/2010 | Corzani et al. |
| 2010/0127432 A1 | 5/2010 | Wagenaar |
| 2010/0205851 A1 | 8/2010 | Uptain et al. |
| 2010/0212214 A1 | 8/2010 | Wu et al. |
| 2010/0251671 A1 | 10/2010 | Thompson et al. |
| 2011/0045424 A1 | 2/2011 | Litten-Brown et al. |
| 2011/0250151 A1 | 10/2011 | Mateu et al. |
| 2011/0274643 A1 | 11/2011 | Yontz |
| 2011/0305042 A1 | 12/2011 | Liwei |
| 2012/0015312 A1 | 1/2012 | Kodali |
| 2012/0222347 A1 | 9/2012 | Clock et al. |
| 2013/0012093 A1 | 1/2013 | Bond |
| 2013/0071799 A1 | 3/2013 | Syed et al. |
| 2013/0150458 A1 | 6/2013 | Iyoku |
| 2013/0158169 A1* | 6/2013 | Bond ............. C08L 23/10 524/51 |
| 2013/0178640 A1 | 7/2013 | Mujkic et al. |
| 2013/0270474 A1 | 10/2013 | Cagle |
| 2014/0041525 A1 | 2/2014 | Morrow |
| 2014/0087941 A1 | 3/2014 | Allen, Jr. et al. |
| 2014/0154197 A1 | 6/2014 | Swaile |
| 2014/0199646 A1 | 7/2014 | Beadles |
| 2014/0273169 A1 | 9/2014 | Scheer et al. |
| 2014/0338134 A1 | 11/2014 | Prieto et al. |
| 2014/0360912 A1 | 12/2014 | Constantine et al. |
| 2015/0164920 A1 | 6/2015 | Soler Ranzani et al. |

FOREIGN PATENT DOCUMENTS

| | | |
|---|---|---|
| EP | 706790 B1 | 7/1997 |
| EP | 745371 B1 | 12/1997 |
| EP | 1023890 A1 | 8/2000 |
| EP | 0953335 B1 | 1/2002 |
| EP | 1024785 B1 | 1/2003 |
| EP | 1343454 A2 | 9/2003 |
| EP | 1417951 A1 | 5/2004 |
| EP | 1561451 A1 | 8/2005 |
| EP | 1661974 A1 | 5/2006 |
| EP | 1671614 A1 | 6/2006 |
| EP | 1556313 B1 | 12/2006 |
| EP | 1813267 A1 | 8/2007 |
| EP | 1455722 B1 | 1/2008 |
| EP | 2020993 A2 | 2/2009 |
| EP | 2030609 A2 | 3/2009 |
| EP | 1903892 B1 | 4/2009 |
| EP | 0906381 B2 | 7/2009 |
| EP | 1651182 B1 | 11/2009 |
| EP | 1345632 B1 | 2/2010 |
| EP | 1660027 B1 | 2/2010 |
| EP | 2173548 A1 | 4/2010 |
| EP | 1791532 B1 | 5/2010 |
| EP | 1284128 B2 | 7/2010 |
| EP | 2371919 B1 | 6/2012 |
| EP | 2309987 B1 | 8/2012 |
| EP | 1942875 B1 | 8/2015 |
| EP | 1974030 B1 | 9/2016 |
| ES | 2328344 T3 | 11/2009 |
| GB | 1351594 A | 5/1974 |
| GB | 2029836 A | 3/1980 |
| GB | 2199246 A | 7/1988 |
| GB | 2419599 A | 5/2006 |
| GB | 2420348 A | 5/2006 |
| WO | 8906269 A1 | 7/1989 |
| WO | WO9931206 A1 | 6/1999 |
| WO | WO9931207 A1 | 6/1999 |
| WO | 0001416 A1 | 1/2000 |
| WO | 0108872 A1 | 2/2001 |
| WO | 2001083656 A1 | 11/2001 |
| WO | WO03022979 A1 | 3/2003 |
| WO | 2010116385 A2 | 10/2010 |
| WO | 2010125342 A2 | 11/2010 |
| WO | 2010143207 A1 | 12/2010 |
| WO | 2011028744 A1 | 3/2011 |
| WO | 2011030351 A2 | 3/2011 |
| WO | 2011079163 A1 | 6/2011 |
| WO | 2011089395 A1 | 7/2011 |
| WO | 2015026906 A1 | 2/2015 |

OTHER PUBLICATIONS

"Homogenize", Random House Unabridged Dictionary, Random House, Inc. 2018, accessed at dictonary.com on Jun. 27, 2018. (Year: 2018).*

"Industrial Starches", Archer Daniels Midland Company, 2018, accessed at adm.com on Jun. 27, 2018. (Year: 2018).*

"Melt Spinning", Huddersfield Textiles,Textile Centre of Excellence, 2018, accessed at tikp.co.uk on Jun. 27, 2018. (Year: 2018).*

WPI World Patent Information Derwent, vol. 13. No. 81, Feb. 5, 1981, XP002091977, 1 page.

International Search Report and Written Opinion, International Application No. PCT/US2017/036945, dated Oct. 19, 2017, 10 pages.

Schroeder, "New Developements in Twin Screw Compounding", Coperion, Bulk Solids Handling & Extrusion Seminars, Riyadh & Dubai, Apr. 2013, 49 pages.

Muhammad Pervaiz et al., "Development of Novel Wax-enabled Thermoplastic Starch Blends and Their Morphological, Thermal and Environmental Properties," International Journal of Composite Materials, vol. 4, No. 5, 2014, XP002768375. p. 204-p. 212.

International Search Report issued in corresponding International Application No. PCT/US2017/014496, dated Mar. 31, 2017, 4 pages.

Written Opinion of the International Search Authority issued in corresponding International Application No. PCT/US2017/014496, dated Mar. 31, 2017, 6 pages.

* cited by examiner

EXTRUDED WAX MELT AND METHOD OF PRODUCING SAME

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure generally relates to a wax melt for use in a wax warmer, and more specifically, to a process of producing wax melts.

2. Description of the Background of the Invention

Typical wickless candle solutions include a warmer and a plurality of wax beads designed to be heated therein. Typical warmers include non-electric warmers such as those heated by tea lights or votive candles and electric warmers that may include a resistive heating element. The wax beads are usually provided in a container or bag that requires the consumer to tilt and/or pour the wax beads into the warmer. The wax beads are frequently very small and may be susceptible to spilling during this process. Further, consumers frequently must purchase a significant quantity of wax beads to provide the same fragrancing benefits as a traditional candle due to the smaller size of the beads.

In other instances, a typical wickless candle solution includes an electric or non-electric warmer and one or more wax melts. The wax melts are usually paraffin or vegetable based. Further, typical wax melts are designed to have a reasonably long shelf life so that the wax melts can be produced, shipped, and positioned in a store for a future sale. To make typical wax melts, each component, including any stabilizers, is heated and blended together. After blending, the molten wax is sprayed into beads and pressed into a mold to form the wax melt. This process is typically referred to as compression molding. Alternatively, wax melts can be produced with a pour process with the wax melt components or ingredients melted together into a liquid and poured into individual molds.

However, some drawbacks exist with these processes. In particular, the process of producing wax melts is energy and effort intensive. The number of steps in production and the constraints presented by a compressed molding operation or pour process present high production costs per unit. As a result, the overall cost of using wax melts is higher than desired.

Therefore, a need exists for a wax melt that is simpler and more cost effective to produce.

SUMMARY OF THE INVENTION

The present disclosure overcomes some of the aforementioned drawbacks by providing a wax melt that is formed using an extrusion process to form a blank of wax melt. The blank can later be cut into individual wax melts.

According to one aspect, a wax melt blank is produced with an extrusion process and intended to later be cut to length into individual wax melts. The wax melt blank includes at least about fifty percent by weight of wax, a fragrance, and up to about fifty percent by weight of a filler. The wax, the fragrance, and the filler are homogeneously dispersed.

According to another aspect, a wax melt blank includes at least about fifty percent by weight of wax, a fragrance, and up to about thirty percent by weight of a filler. The wax melt blank is made by a process that includes the steps of introducing the filler to a first stage of a twin screw extrusion system, introducing the fragrance oil to the first stage, mixing the filler and the fragrance oil in the first stage, introducing the wax in a second stage of the twin screw extrusion system, mixing the filler, the fragrance oil, and the wax in a third stage of the twin screw extrusion system to form a mixture, and forcing the mixture through a die to form the wax melt blank.

According to a further aspect, a method of producing a wax melt blank that includes at least about fifty percent by weight of wax, a fragrance, and up to about thirty percent by weight of a filler is disclosed. The method includes the steps of introducing the filler to a first stage of a twin screw extrusion system, introducing the fragrance oil to the first stage, mixing the filler and the fragrance oil in the first stage, introducing the wax in a second stage of the twin screw extrusion system, mixing the filler, the fragrance oil, and the wax in a third stage of the twin screw extrusion system to form a mixture, and forcing the mixture through a die to form the wax melt blank.

According to another aspect, a wax melt blank is produced with an extrusion process and intended to later be cut to length into individual wax melts. The wax melt blank includes at least fifty percent by weight of wax, a fragrance, and up to thirty percent by weight of a filler. The wax, the fragrance, and the filler are homogeneously dispersed.

According to a further aspect, a method of producing a wax melt includes the steps of providing a filler to an extrusion system, providing a fragrance to an extrusion system, mixing the filler with the fragrance, providing a wax to the filler and the fragrance within the extrusion system after mixing the filler with the fragrance, homogenizing the filler, the fragrance, and the wax, and extruding the homogenized filler, fragrance, and wax through a die to form an extruded wax melt blank.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

Figure 1:
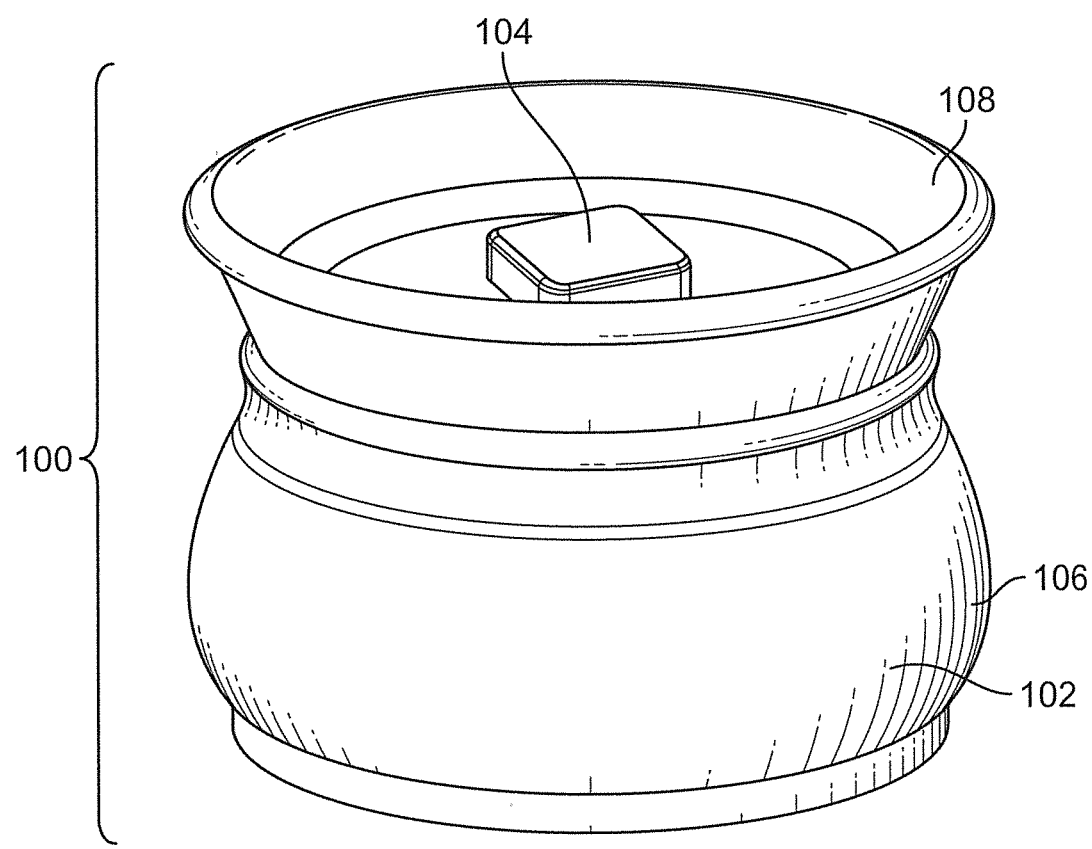
FIG. 1 is an isometric view of a wax melt system including an electric warmer and a wax melt according to a first embodiment.

With reference to FIG. 1, one particular embodiment of a wax melt system 100 is illustrated that generally includes a wax warmer 102 designed to accommodate one or more wax melts 104. One or more components of the wax melt system 100 may be sold separately or as part of a kit. It is envisioned that the wax melt system 100 described herein includes at least one wax melt 104 that is devoid of a wick (e.g., wickless). Additionally, it is envisioned that the melting process of the wax melt 104 may be accomplished via means that do not include a flame directly adjacent thereto.

As shown in FIG. 1, the wax warmer 102 generally includes a body 106, a reservoir 108, and a heater assembly (not shown) disposed therein. The body 104 is designed to act as a support structure for the reservoir 108 and enclose internal components thereof (e.g., the heater assembly). The wax warmer 102 includes a power source (not shown) that is provided in the form of an electrical power cord, a battery, a tealight, and/or another power source that provides energy thereto. The wax warmer 102 may be characterized by any structure that provides a surface designed to transfer heat from the wax warmer 102 to the wax melt 104.

The following discussion is directed to production of wax melts 104 via an extrusion process. Extrusion provides a number of advantages over the compression molding and pour molding processes typically used in the production of wax melts. Extrusion provides a continuous blank of wax melt material that can be later cut to length and reduces the number of steps in the production process. Additionally, extrusion can utilize wax in molten form greatly reducing the cost of production. Extrusion combines the process of material combination, kneading, and formation into a single step. Extrusion is also more energy efficient than typical compression molding operations and pour processes.

Figure 2:
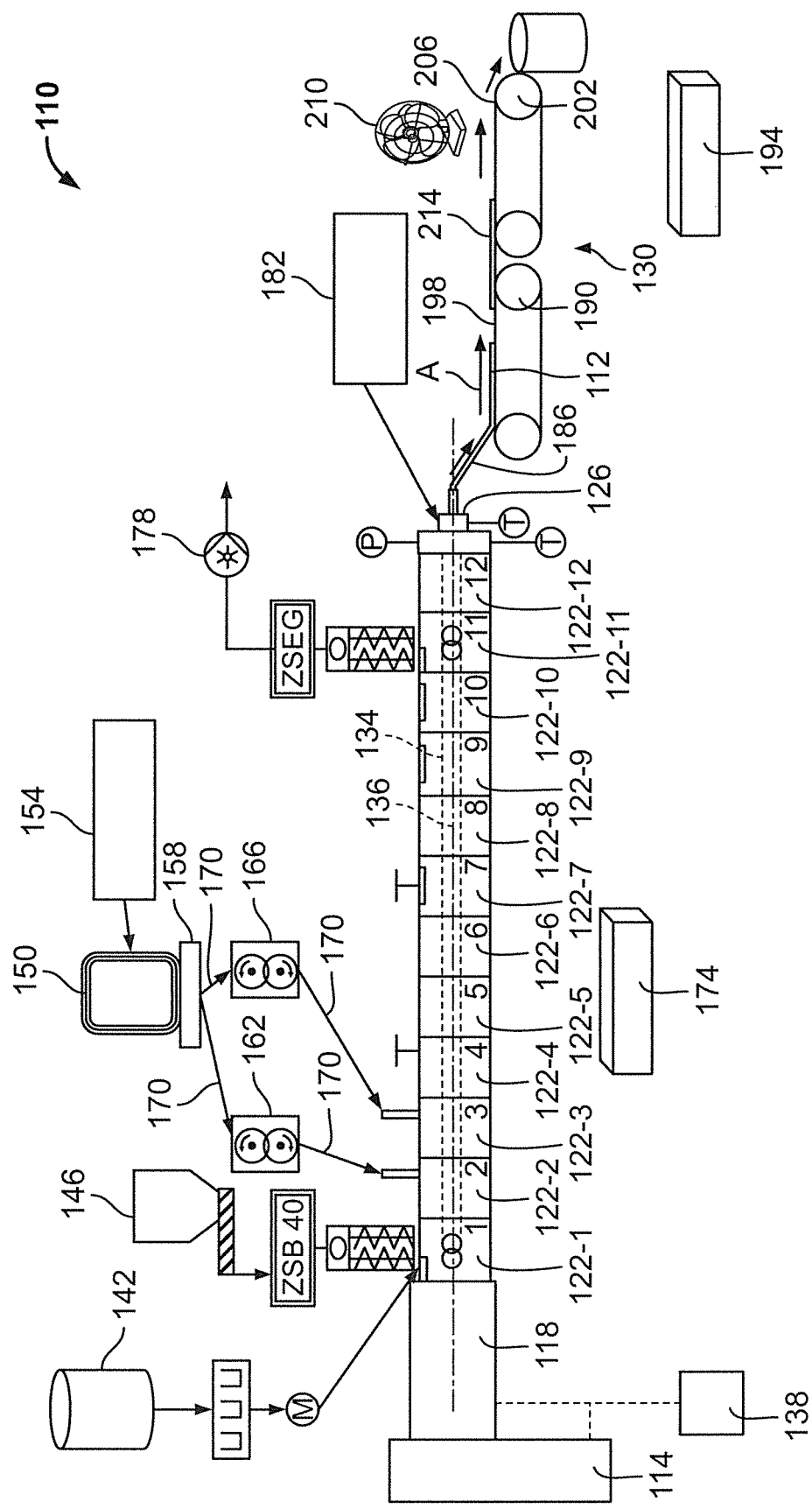
FIG. 2 is a schematic view of an extrusion system for producing the wax melt of FIG. 1.
Figure 3:
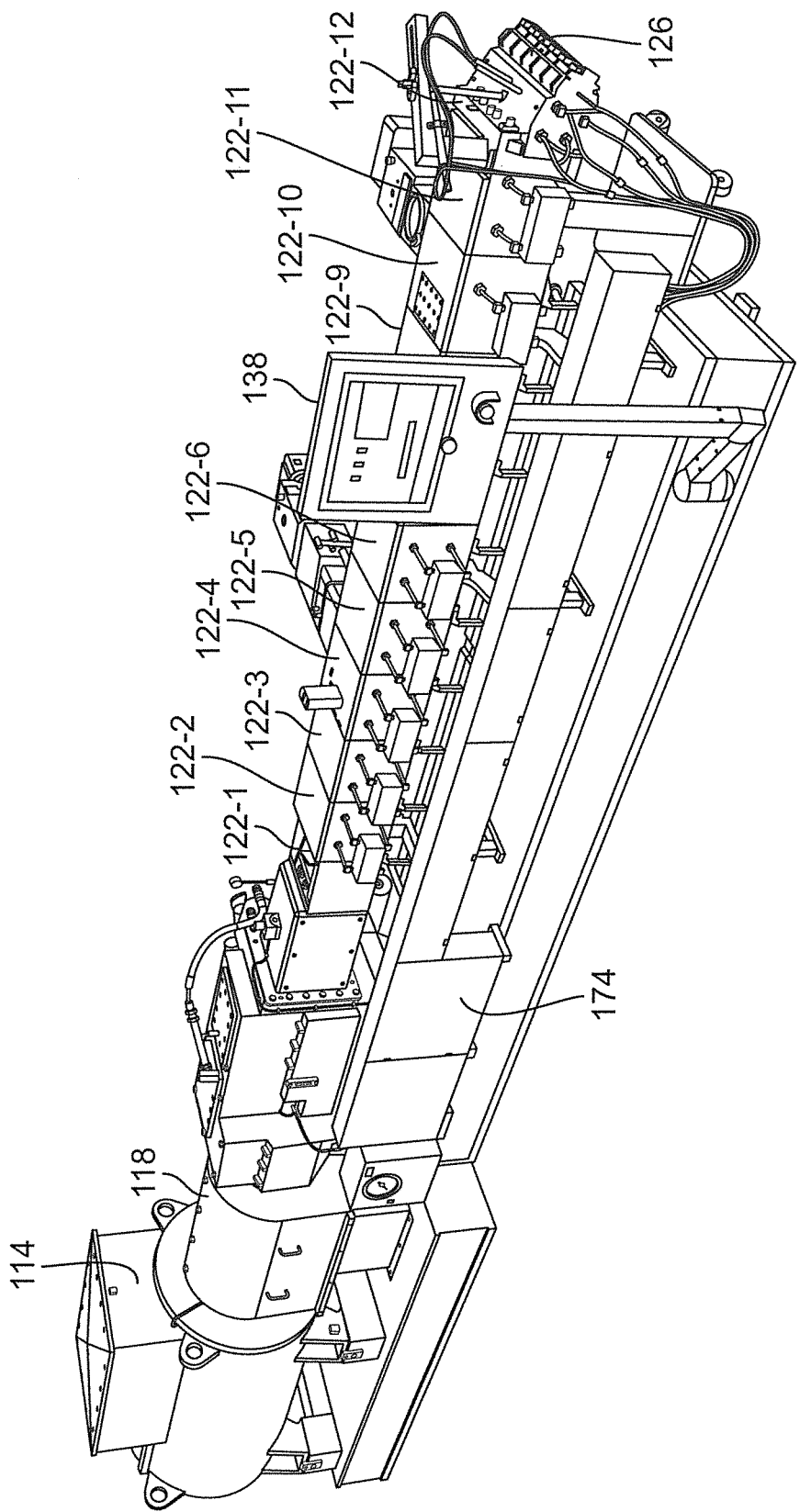
FIG. 3 is a perspective view of an extruder of the extrusion system of FIG. 2.

As shown in FIG. 2, an extrusion system 110 arranged to produce a continuous blank of extruded wax melt 112 generally includes a drive 114, a transmission 118, first through twelfth extrusion stages 122-1-12, a die 126, and a conveyor system 130. In one instance, as shown in FIG. 3, the extrusion system is a customized ZSK 45 MC18 produced by Coperion Corporation, of Stuttgart, Germany. In other instances, other extrusion machines may be used to match desired production throughput, or operation characteristics.

The drive 114 powers the transmission 118, which in turn rotates a pair of screws 134 arranged within the first through twelfth stages 122-1-12 (see FIG. 2). Each of the screws 134 defines a longitudinal axis that extends parallel to an extrusion axis 136. The screws 134 are arranged such that the extrusion process progresses in a direction generally extending along the extrusion axis 136. That is to say, as the extrusion process proceeds, components of the extruded wax melt 112 are added and processed within the extrusion stages 122-1-12 in various ways (e.g., mixing, kneading, compressing, etc.) and move generally in a direction along the extrusion axis 136 from the first stage 122-1 toward the twelfth stage 122-12. The drive 114 and transmission 118 are controlled by a controller 138 that dictates the speed of rotation of the screws 134. In one instance, the screws 134 are rotated at about 1,200 rpm (one-thousand two hundred rotations per minute). In other instances, different rotational speeds may be utilized to produce a desired throughput and desirable processing characteristics.

A source of fragrance in the form of a fragrant oil blend 142 is coupled to the first stage 122-1. In one instance, the fragrant oil blend 142 is provided to the first stage 122-1 at a rate of about fifteen to forty-five pounds per hour (15-45 lb/hr). In other constructions, a different amount or rate of fragrance is provided to the extrusion system 110.

A source of filler in the form of cornstarch 146 is also coupled to the first stage 122-1. In one instance, the cornstarch 146 is provided to the first stage 122-1 at a rate of about twenty to one-hundred-eighty pounds per hour (20-180 lb/hr). In other constructions, a different amount or rate of filler is provided to the extrusion system 110.

A source of wax in the form of molten wax 150 is coupled to the second stage 122-2 and the third stage 122-3. Molten wax 150 may be brought to a production facility in tankers via train or truck and present a significant cost savings over bead wax or blocks of wax that must be melted on site or in the extrusion process. In one instance, using molten wax 150 presents a ten percent (10%) cost savings relative to bead wax. In other constructions, the source of wax may be beads or bricks of wax that are melted on site. While not as efficient, these and other sources of wax may be advantageous depending on the location or arrangement of an overall production facility.

A heater 154 is arranged to maintain the molten wax 150 at a workable temperature. For example, the molten wax 150 is maintained at about one-hundred-fifty-five to one-hundred-seventy degrees Fahrenheit (155-170° F.). In other constructions, a different temperature may be preferred to maintain the selected wax blend in a workable molten state. A scale or meter 158 routes the molten wax 150 to a first feed device 162 arranged to provide a predetermined amount of molten wax 150 to the second stage 122-2, and a second feed device 166 arranged to provide a predetermined amount of the molten wax 150 to the third stage 122-3. Lines 170 connecting the meter 158, the first feed device 162, the second feed device 166, the second stage 122-2, and the third stage 122-3 are jacketed and warmed by, for example, heat lamps such that the molten wax 150 within the lines 170 is provided to the second stage 122-2 and the third stage 122-3 in a workable state. In one instance, a total amount of molten wax 150 provided by the sum of the first feed device 162 and the second feed device 166 is about one-hundred-forty to three-hundred-fifty pounds per hour (140-350 lb/hr). In one instance, the first feed device 162 is a gear pump with a capacity of about fifty cubic centimeters (50 cc) and the second feed device 166 is a gear pump with a capacity of about twenty cubic centimeters (20 cc). In other constructions, the molten wax 150 may be provided at a different rate or in different amounts. Additionally, the feed devices may be arranged differently. For example, an equal amount of molten wax 150 may be fed to the second stage 122-2 and the third stage 122-3.

A cooling unit 174 is in communication with stages four through twelve 122-4-12. The cooling unit 174 can be a liquid cooling unit that provides chilled fluid (e.g., glycol) to jackets surrounding at least a portion of each of the stages four through twelve 122-4-12. The cooling unit 174 removes heat from the extruder stages 122-4-12 as the mixture of the molten wax 150, the fragrant oil blend 142, and the cornstarch 146 progresses. The cooling unit 174 improves the uniformity of the finished continuous blank of extruded wax melt 112. Eliminating the cooling unit 174 may lead to non-uniform surface features such as railroad track like indentations on the surface of the continuous blank of extruded wax melt 112.

A vacuum system 178 is in communication with the eleventh stage 122-11 and applies a vacuum to the mixture of the molten wax 150, the fragrant oil blend 142, and the cornstarch 146 through a single screw port as it passes through the eleventh stage 122-11. The vacuum system 178 reduces the amount of entrapped air within the mixture. In one embodiment, the vacuum system 178 applies only the minimum level of vacuum required to give the extruded wax melt 112 a uniformly smooth surface appearance and a uniform cross section. Additionally, the minimum level of vacuum should substantially eliminate large air bubbles within the extruded wax melt 112. Alternatively, the vacuum system 178 may be replaced with an atmospheric vent.

The die 126 is coupled to the twelfth stage 122-12 and is shaped to form the desired wax melt profile. The die 126 is heated, for example, by a resistive heater 182 that maintains the temperature of the die 126 at about one-hundred-twenty to about one-hundred-thirty degrees Fahrenheit (120-130° F.). In other constructions, the die 126 is maintained at about one-hundred-thirty-five to about one-hundred-fifty-five degrees Fahrenheit (135-155° F.). The resistive heater 182 provides heat to the die 126 and improves the surface texture of the extruded wax melt 112.

An optional ramp 186 may be arranged to support extruded wax melt 112 as it exits the die 126 and guide the extruded wax melt 112 to the conveyor system 130. In some instances, the ramp 186 may be eliminated and the extruded wax melt 112 may exit the die 126 directly onto the conveyor system 130. In other instances, the ramp 186 may be rotatably mounted such that the ramp 186 supports the continuous blank of extruded wax melt 112 upon startup, but is removed once the extrusion process reaches steady state.

The conveyor system 130 includes a chilled conveyor 190 that conveys the extruded wax melt 112 in a first direction A. In one instance, the direction A is parallel with the extrusion axis 136. In a particular instance, the chilled conveyor 190 includes a stainless steel conveying surface 198 provided by, for example, Sandvik Process Systems, of Stockholm, Sweden. A conveyor cooling unit 194 provides cooling fluid to the underside of the chilled conveyor 190. This removes heat from the extruded wax melt 112 while not bringing the extruded wax melt 112 into contact with the cooling fluid. In one instance, the cooling fluid is water maintained between about forty-five and sixty-five degrees Fahrenheit (45-65° F.). In other instances, other temperatures may be utilized recognizing that the warmer the cooling fluid is, the slower the extrusion process will run and/or an increased cooling post extrusion will be required.

The conveyor system 130 also includes an outfeed conveyor 202 that receives the extruded wax melt 112 from the chilled conveyor 190 and continues to convey the extruded wax melt 112 in the first direction A. In one instance, the outfeed conveyor 202 includes a canvas conveying surface 206 provided by, for example, Kamflex Corporation, of Chicago Ill. An air cooling system in the form of a fan 210 may be provided to blow air across the extruded wax melt 112 as it is conveyed in the first direction A. The blowing air further removes heat from the extruded wax melt 112 and helps the extruded wax melt 112 set in shape.

The conveyor system 130 further includes a transition plate 214 arranged between the chilled conveyor 190 and the outfeed conveyor 202. The transition plate 214 limits the deflection experienced by the extruded wax melt 112 as it transfers from the chilled conveyor 190 to the outfeed conveyor 202.

In some instances, the conveyor system 130 can include a cooling tunnel that substantially surrounds the conveyor system 130 with cooled air. For example, the cooling tunnel could encompass the chilled conveyor 190 and the outfeed conveyor 202, such that the extruded wax melt 112 is cooled from below by the chilled conveyor 190 and from above along substantially the entire length of the conveyor system 130.

Figure 4:
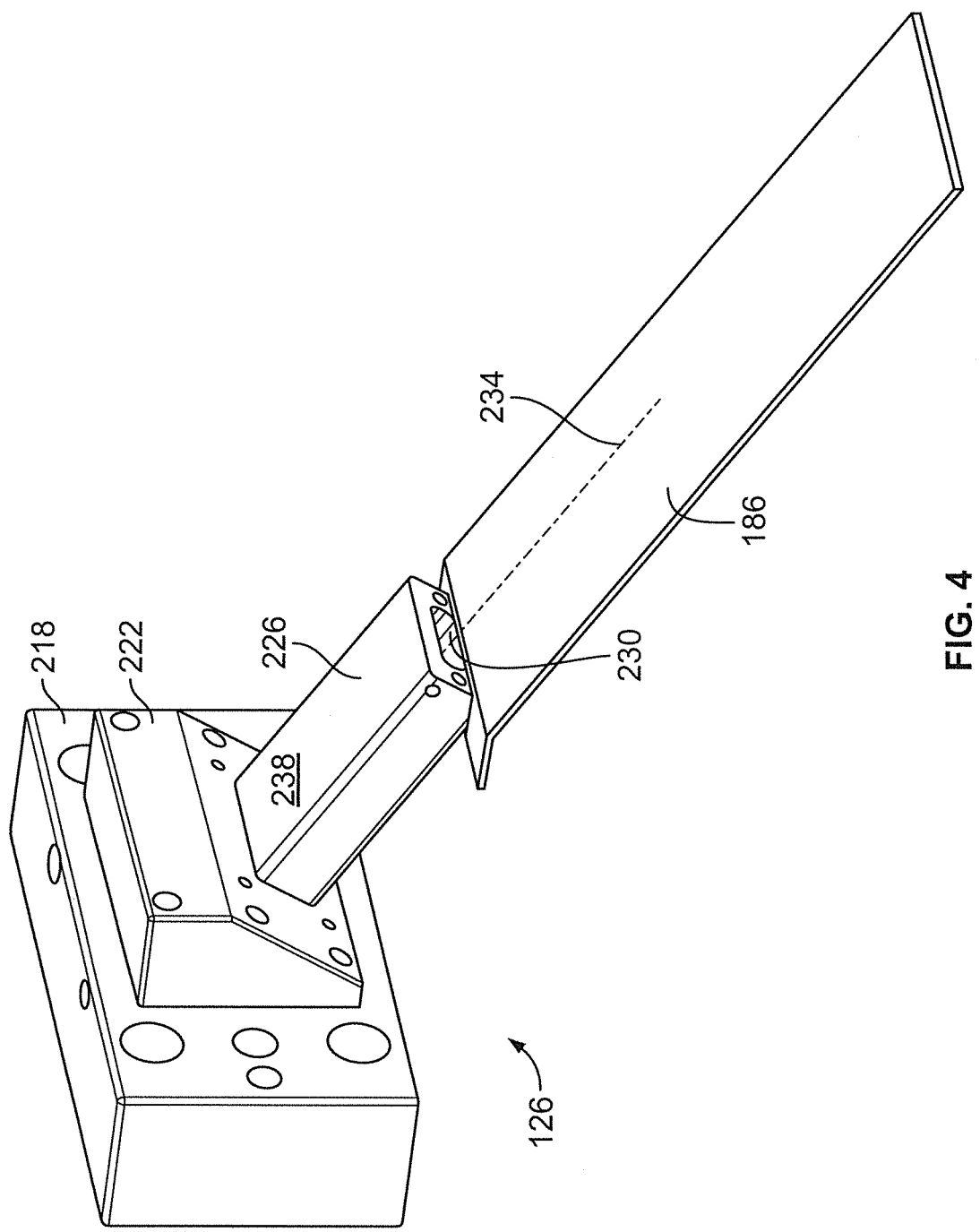
FIG. 4 is an isometric view of a die assembly of the extruder of FIG. 3.

FIG. 4 shows one example of the die 126 and option ramp 186. The die 126 may be fabricated from a 400 series stainless steel and includes a mounting block 218 arranged to mount onto the twelfth stage 122-12 with fasteners, a coupling block 222 fastened to the mounting block 218, and a die head 226. The mounting block 218 and the coupling block 222 are connected to the cooling unit 174 and receive cooled fluid to remove heat from the system. The die head 226 defines a die passage 230 that defines a die axis 234. The die axis 234 is arranged at an oblique angle relative to the extrusion axis 136. In one instance, the die axis 234 is arranged at an angle of about thirty degrees (30°) relative to the extrusion axis 136. In other instances, the die angle may be different as desired. For example, die angles between about zero degrees and about forty-five degrees (0-45°) may be advantageous.

The die head 226 provides an outer surface 238 that is arranged to receive the resistive heater 182. In other instances, the resistive heater 182 may be replaced by another heater arranged to heat the die head 226 to a suitable degree. For example, resistive or inductance heaters may be arranged within the die head 226, or fluid heating may be utilized, as desired. The resistive heater 182 helps improve the surface smoothness of the extruded wax melt 112 as is exits the die head 226.

Figure 5:
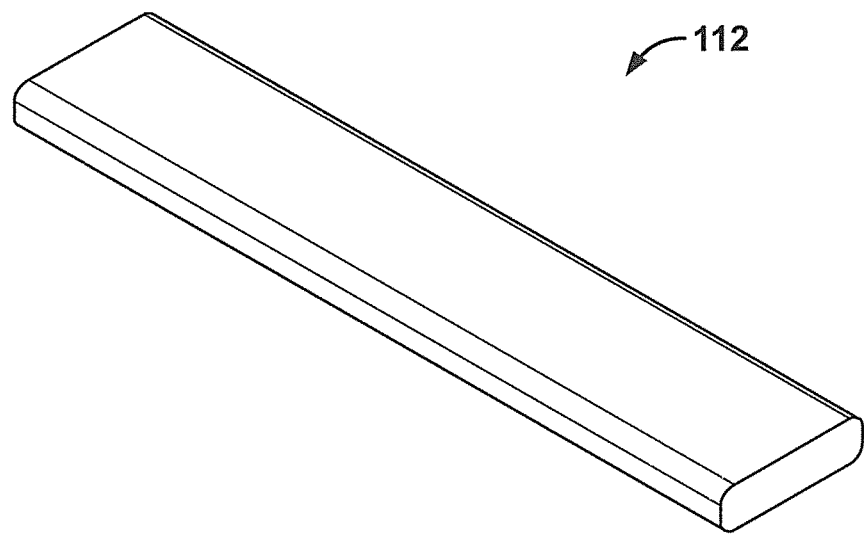
FIG. 5 is an isometric view of a wax melt blank produced using the extrusion system of FIG. 2.
Figure 6:
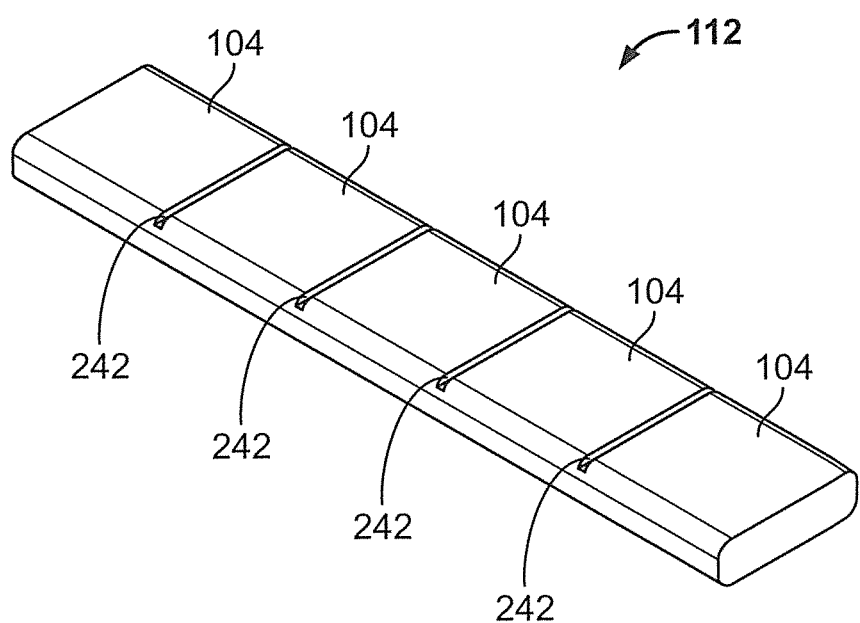
FIG. 6 is an isometric view of a scored wax melt blank produced using the extrusion system of FIG. 2.

The extrusion system 110 discussed above is arranged to produce a continuous blank of extruded wax melt 112 that has a consistent cross sectional profile that defines a width of about one-and-one-half inches (1.5") and a height of about 0.425 inches. In other instances, the extruded wax melt may have other dimensions, as desired. After the continuous blank of extruded wax melt 112 is produced, it is cut to length as shown in FIG. 5, then scored with scoring marks 242 as shown in FIG. 6, such that an end user can easily break off a singular wax melt 104 for use in a wax warmer 102. Alternatively, the continuous blank of extruded wax melt 112 can be cut into individual wax melts 104 that are packaged together and sold.

The extrusion system 110 discussed above is only one example of a system that is suitable for extruding a continuous blank of extruded wax melt 112. For example, in place of the molten wax 150, the source of wax may be preformed bead wax that is added directly to the third stage 122-3, or melted before addition to the extrusion system 110. In one instance, the source of wax includes a paraffin wax. In another instance, the source of wax includes a mixture of waxes including paraffin wax. For example, a mixture of about eighty-five percent (85%) Parafflex 4800 series wax and about fifteen percent (15%) Microsere 5897A microcrystalline wax may be used. In another instance, a different wax or a different wax blend may be utilized. For example, a vegetable based wax, such as soy wax, may be used. For the finished wax melt 104 to melt normally and function as desired by the end user, the wax or blend of waxes should make up at least fifty percent (50%) by weight of the composition of the finished wax melt 104. In one instance, the wax or blend of waxes makes up between about fifty percent (50%) and about eighty percent (80%) by weight of the total composition of the finished wax melt 104.

In the embodiment discussed above the filler is cornstarch 146. For example, the cornstarch 146 can be a powdered form. Alternatively, the filler can be talc or a wood fiber. In one instance, the filler is added to the first stage 122-1 with a feeder screw such as the K-Tron T35 offered by Coperion Corporation, of Stuttgart, Germany. In one instance, the filler makes up between about ten percent (10%) and about fifty percent (50%) by weight of the total composition of the finished wax melt 104. Counter to common knowledge, the addition of a filler, in particular cornstarch 146, increases the strength of the continuous blank of extruded wax melt 112. Typically, the addition of fillers to extruded products reduces the strength. The addition of the cornstarch 146 also improves the texture or smoothness of the continuous blank of extruded wax melt 112 and increases the plasticity. Below about ten percent (10%) by weight, the extruded wax melt 112 is too liquid and fails to hold shape after exiting the die 126. In other words, when the filler makes up less than about ten percent (10%) of the composition slumping and suboptimal contraction takes place, which leads to a continuous blank of extruded wax melt 112 that does not meet aesthetic tolerances. Above thirty percent (30%) by weight of filler, the continuous blank of extruded wax melt 112 becomes more brittle and exhibits some cracking on the surface of the continuous blank of extruded wax melt 112. In one instance, the amount of filler added to the continuous blank of extruded wax melt 112 is between about twenty-five percent (25%) and about thirty percent (30%) by weight. The amount of filler included in the mixture affects the shrink rate of the continuous blank of extruded wax melt 112 upon cooling after exiting the die 126. The shrinkage must be accounted for during production layout and planning. Additionally, the filler helps to remove heat from the system because the cornstarch 146 (for example) is added at a temperature below the temperature of the molten wax 150. This reduces the cooling load on the cooling unit 174.

In one embodiment, the fragrant oil blend 142 is added to the first stage 122-1 with a diaphragm pump such as the Lewa EK-3-10 offered by Lewa GmbH, of Leonburg, Germany. The fragrant oil blend 142 may be in a liquid form. The amount of fragrance oil blend 142 added to the continuous blank of extruded wax melt 112 is below about 30 percent (30%) by weight of the total composition. In one instance, the amount of fragrance oil blend 142 added to the continuous blank of extruded wax melt 112 is between about four percent (4%) and about ten percent (10%) by weight. Above thirty percent (30%) by weight, the fragrance oil blend 142 has a tendency to seep or leak out of the continuous blank of extruded wax melt 112.

The first through twelfth stages 122-1-12 of the extrusion system 110 are designed to mix the composition but not to aggressively knead the mixture. Kneading stages increase the heat build up within the mixture and require more cooling and risk deterioration of the extruded wax melt 112. Additionally, aggressive kneading can lead to more entrapped air.

Any of the embodiments described herein may be modified to include any of the structures or methodologies disclosed in connection with different embodiments. Further, the present disclosure is not limited to wax warmers, wax melts, or extrusion machines of the type specifically shown. Still further, the wax melts of any of the embodiments disclosed herein may be modified to work with any type of warmer that utilizes wax melts or the like.

INDUSTRIAL APPLICABILITY

A wax melt is presented that is heated by a wax warmer for dispensing material into the surrounding environment. The wax melt is produced by an extrusion process. The extrusion process involves first forming a continuous blank of extruded wax melt and then subsequently scoring and cutting the continuous blank of extruded wax melt into individual wax melts.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A method of producing a wax melt blank including at least fifty percent by weight of wax, a fragrance oil, and up to about thirty percent by weight of a filler, the method comprising:
   introducing the filler to a firs stage of a twin screw extrusion system;
   introducing the fragrance oil to the first stage;
   mixing the filler and the fragrance oil in the first stage;
   introducing the wax in a second stage of the twin screw extrusion system;
   mixing the filler, the fragrance oil, and the wax in a third stage of the twin screw extrusion system to form a mixture; and
   forcing the mixture through a die to form the wax melt blank.

2. The method of claim 1, further comprising introducing the filler at room temperature.

3. The method of claim 1, further comprising introducing the wax in the third stage of the twin screw extrusion system.

4. The method of claim 1, further comprising applying a vacuum to the mixture before forcing the mixture through the die.

5. The method of claim 1, further comprising cooling the twin screw extrusion system between the first stage and the die.

6. The method of claim 1, wherein introducing the wax includes introducing molten wax.

7. The method of claim 1, further comprising heating the die with a resistive element.

8. The method of claim 1, further comprising cooling a mounting block of the die.

9. The method of claim 1, further comprising the wax melt blank exiting the die at an angle with respect to an extrusion axis.

10. The method of claim 1, further comprising receiving the wax melt blank on a chilled conveyor.

11. The method of claim 1, wherein introducing the filler includes introducing cornstarch.

12. A method of producing a wax melt blank, the method comprising:
   providing a filler to an extrusion system, wherein the filler is a talc or a wood fiber;
   providing a fragrance to the extrusion system;
   mixing the filler with the fragrance;
   providing a wax to the filler and the fragrance within the extrusion system after mixing the filler with the fragrance;
   homogenizing the filler, the fragrance, and the wax in the extrusion system while removing heat from the extrusion system; and
   extruding the homogenized filler, fragrance, and wax through a die to form an extruded wax melt blank comprising at least fifty percent by weight of the wax, the fragrance, and between ten percent and thirty percent by weight of the filler.

13. The method of claim 12, further including the steps of:
cooling the extruded wax melt blank; and
cutting the cooled wax melt blank to length.

14. The method of claim 13, wherein cooling the extruded wax melt blank includes receiving the extruded wax melt blank from the die and supporting the extruded wax melt blank on a cooled conveyor.

15. The method of claim 13, wherein cooling the extruded wax melt blank includes forcing air over the extruded wax melt blank.

16. The method of claim 13, wherein cutting the cooled wax melt blank to length includes scoring a surface of the cooled wax melt blank.

\* \* \* \* \*